United States Patent
Nakamura et al.

(10) Patent No.: US 9,815,827 B2
(45) Date of Patent: *Nov. 14, 2017

(54) AGENT FOR TREATMENT OF SCHIZOPHRENIA

(71) Applicant: Sumitomo Dainippon Pharma. Co., Ltd., Osaka-shi, Osaka (JP)

(72) Inventors: Mitsutaka Nakamura, Kawanishi (JP); Masaaki Ogasa, Tokyo (JP); Shunsuke Sami, Kawasaki (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 184 days.

This patent is subject to a terminal disclaimer.

(21) Appl. No.: 14/471,919

(22) Filed: Aug. 28, 2014

(65) Prior Publication Data

US 2014/0371236 A1    Dec. 18, 2014

Related U.S. Application Data

(63) Continuation of application No. 10/525,021, filed as application No. PCT/JP03/10490 on Aug. 20, 2003, now Pat. No. 9,174,975.

(60) Provisional application No. 60/404,927, filed on Aug. 22, 2002.

(51) Int. Cl.
C07D 417/12    (2006.01)
A61K 31/496    (2006.01)

(52) U.S. Cl.
CPC .......... *C07D 417/12* (2013.01); *A61K 31/496* (2013.01)

(58) Field of Classification Search
CPC ............................ A61K 31/496; C07D 417/12
See application file for complete search history.

(56) References Cited

U.S. PATENT DOCUMENTS

| | | | |
|---|---|---|---|
| 5,444,073 A | 8/1995 | Perregaard et al. | |
| 5,532,372 A | 7/1996 | Saji et al. | |
| 5,780,632 A | 7/1998 | Saji et al. | |
| 6,964,962 B2 * | 11/2005 | Wong | A61K 31/519 514/220 |
| 7,067,507 B2 | 6/2006 | Pulley et al. | |
| 2001/0047010 A1 * | 11/2001 | Pozuelo | A61K 31/44 514/310 |
| 2003/0050307 A1 | 3/2003 | Ruhland et al. | |
| 2006/0025422 A1 | 2/2006 | Nakamura et al. | |
| 2006/0111429 A1 | 5/2006 | Fish et al. | |
| 2006/0142276 A1 | 6/2006 | Ohno et al. | |
| 2008/0255148 A1 | 10/2008 | Ohno et al. | |
| 2009/0176800 A1 | 7/2009 | Ishiyama | |
| 2010/0105692 A1 | 4/2010 | Moheno et al. | |

FOREIGN PATENT DOCUMENTS

| | | |
|---|---|---|
| EP | 4 648 46 A1 | 1/1992 |
| JP | 05-17440 A | 1/1993 |
| JP | 6-504787 A | 6/1994 |
| JP | 08-333368 | 12/1996 |
| JP | 2000-281576 | 10/2000 |
| JP | 2003-135074 A | 5/2003 |
| JP | 2003-160583 | 6/2003 |
| JP | 2003-519226 A | 6/2003 |
| WO | WO 93/16073 | 8/1993 |
| WO | WO 95/34306 | 12/1995 |
| WO | WO 96/14297 | 5/1996 |
| WO | WO 99/52519 | 10/1999 |
| WO | WO 02/22581 A1 | 3/2002 |
| WO | WO 02/24166 A1 | 3/2002 |
| WO | WO 03/066039 A1 | 8/2003 |
| WO | WO 2004/017973 | 3/2004 |
| WO | WO 2004/113333 | 12/2004 |
| WO | WO 2007/124757 A2 | 11/2007 |
| WO | WO 2008/124030 | 10/2008 |

OTHER PUBLICATIONS

Alphs, Larry, "An industry perspective on the NIMH Consensus Statement on negative symptoms," Schizophrenia Bulletin, vol. 32, No. 2, pp. 225-230, (2006).
Approval Labeling Text, NDA 21-487, for NAMENDA™ (memantine hydrochloride) (2003).
Barber, Teresa A., et al., "Memantine ameliorates scopolamine-induced amnesia in chicks trained on taste-avoidance learning," Neurobiology of Learning and Memory, vol. 93, pp. 540-545, (2010).
Bejar, Corina, et al., "Effect of rivastigmine on scopolamine-induced memory impairment in rats," European Journal of Pharmacology, vol. 383, pp. 231-240, (1999).
Biederman, Joseph, et al., "Risperidone treatments for ADHD in children and adolescents with bipolar disorder," Neuropsychiatric Diseases and Treatment, vol. 4, No. 1, pp. 203-207 (2008).
Botero, Hector M. et al., "Structure—Activity Relationships in a Series of Bisquaternary Bisphthalimidine Derivatives Modulating the Muscarinic M2-Receptor Allosterically," J. Med. Chem., vol. 43, pp. 2155-2164, (2000).

(Continued)

*Primary Examiner* — Snigdha Maewall
(74) *Attorney, Agent, or Firm* — Oblon, McClelland, Maier & Neustadt, L.L.P.

(57) ABSTRACT

The present invention provides a novel method for treatment of schizophrenia which can improve wide-ranging symptoms of schizophrenia, especially positive symptoms and negative symptoms without being accompanied by extrapyramidal symptoms, which comprises orally administering as an active compound (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboxyimide or a pharmaceutically acceptable salt thereof (e.g., hydrochloride) at a daily dose of 5 mg to 120 mg once a day to a patient with schizophrenia, and a therapeutic agent to be used in said method.

75 Claims, 1 Drawing Sheet

(56) References Cited

OTHER PUBLICATIONS

Bowen, D.M., "Traditional pharmacotherapy may succeed in alzheimer's disease," Trends in Neurosciences, vol. 15, No. 3, pp. 84-85, (1992).

Bruno, et al., The α2c-adrenergic receptor mediates hyperactivity of colobomo mice, a model of attention deficit hyperactivity disorder, Neurobiology of Disease, vol. 23, pp. 679-688, (2006).

Center for Drug Evaluation and Research, Pharmacology Reviews at FDA, pp. 1-260, (Oct. 2010).

Clinton et al., Altered transcript expression of NMDA, receptor associated postsynaptic proteins in the thalamus of subject with schizophrenia, Am. J. Psychiatry, vol. 160, No. 6, pp. 1100-1109, (Jun. 2003).

Clinton et al., "Thalamic expression of NMDA receptor-associated postsynaptic density proteins in schizophrenia," Society for Neuroscience, Program No. 754.4, (2003), (online) (abstract only).

Cloninger, "The discovery of susceptibility genes for mental disorders," Proc. Natl. Acad. Sci., vol. 99, No. 21, pp. 13365-13367, (Oct. 15, 2002).

Corbett, "Clozapine but not haloperidol antagonizes an MK-801 discriminative stimulus cue," Pharmacol. Biochem. Behav., vol. 51(2-3), pp. 561-564, (1995).

Current Opinion in Neurobiology 2000, 10:205-210, Schizophrenia and cognitive function.

Diagnostic and Statistical Manual of Mental Disorders, Fourth Edition (DSM-IV™) pp. 273-278, 285, and 286 (1994), published by the American Psychiatric Association, Washington, D.C.

"Delirium, Dementia, Amensia, Cognitive Disorders," http://www.nlm.nih.gov/cgi/mesh/2009/MB_cgi?mode=& term. .m,+Dementia,+Amnestic,+Cognitive+Disorders &field=entry, accessed Jul. 1, 2009.

Didriksen, et al., "Antipsychotic potential of the Gly T-1 inhibitor NFPS," Society Neuroscience Abstract, vol. 2002, abstract No. 893.1, (2002).

Doggrell, Sheila A. et al., "Treatment of dementia with neurotransmission modulation," Expert Opinion on Investigational Drugs, vol. 12, No. 10, pp. 1633-1654, (2003).

Duka, Theodora, "Scopolamine-induced amnesia in humans: Lack of effects of the benzodiazepine receptor antagonist β-carboline ZK 93426," Journal of Psychopharmacology, vol. 6, No. 3, pp. 382-388, Abstract, (1992).

Ebihara, Mitsuru et al., "Togo Scicchosho no Dobutsu Model," Igaku no Ayumi, vol. 208, No. 3, pp. 138-142, (2004).

Emre, Murat, M.D. et al., "Rivastigmine for dementia associated with parkinson's disease," The New England Journal of Medicine, vol. 351, No. 24, pp. 2509-2518, (2004).

English translation of Office Action from the Chinese Patent Office in Appln. No. 200480017534.X dated Jan. 29, 2010.

English translation of Office Action from the Japanese Patent Office in Appln. No. 2005-507314 dated Jun. 29, 2010.

English translation of Second Office Action from the Chinese Patent Office in Appln. No. 200480017534.X dated Jan. 29, 2010.

Enomoto et al., "Development of antipsychotics by using animal model," Brain Science, vol. 25, No. 5, pp. 437-444 (2003).

EP Official Action for Corresponding EP Application No. 04 746 564.6-2117 dated Nov. 20, 2009.

EP Official Action for Corresponding EP Application No. 04 746 564.6-2117 dated Aug. 27, 2010.

EP Search Report for European Patent Application No. 04 746 564.6 dated Mar. 2, 2009.

EP Search Report for European Patent Application No. 11160001.1-2123 dated Jul. 19, 2011.

Erhart, Stephen M., et al., "Treatment of schizophrenia negative symptoms: future prospects," Schizophrenia Bulletin, vol. 32, No. 2, pp. 234-237, 2006.

European Neuropsychopharmacology, "P.3.155 Efficacy of lurasidone (SM-13496) in the treatment of schizophrenia: results of two, phase 2, pacebo-controlled studies," vol. 15, pp. S522-S523, (2005).

Fabre, Serge et al., "Protein Kinase C Inhibitors; Structure—Activity Relationships in K252c-Related Compounds," Bioorg. Med. Chem., vol. 1, No. 3, pp. 193-196, (1993).

Fernandez, Hubert H. et al., "Pharmacotherapy of dementia with Lewy bodies," Expert Opinion on Pharmacotherapy, vol. 4, No. 11, pp. 2027-2037, (2003).

Final Office Action in U.S. Appl. No. 12/140,927 dated Jul. 10, 2009.

Final Office Action in U.S. Appl. No. 12/140,927 dated Jul. 18, 2011.

Friedman, Joseph I., "Cholinergic targets for cognitive enhancement in schizophrenia: focus on cholinesterase inhibitors and muscarinic agonists," Psychopharmacology, 174, pp. 45-53, (2004).

Geyer et al., "Animal behavior models of the mechanisms underlying antipsychotic atypicality," Progress in Neuro-Psychopharmacology & Biological Psychiatry, vol. 27, pp. 1071-1079, (2003).

Goff et al., "The emerging role of glutamate in the pathophysiology and treatment of schizophrenia," Am. J. Psychiatry, vol. 158, No. 9, pp. 1367-1377, (Sep. 2001).

Harrod et al., "MK-801 induced retrieval, but not acquisition, deficits for passive avoidance conditioning," Pharmacology, Biochemistry, and Behavior, vol. 69, pp. 585-593, (2001).

Harvey et al., "Cognition in schizophrenia: from basic science to clinical treatment," Psychopharmacology, vol. 169, pp. 213-214, (2003).

Harvey et al., "Cognitive functioning in schizophrenia: a consensus statement on its role in the definition and evaluation of effective treatments for the illness," J. Clin. Psychiatry, vol. 65, pp. 361-372, (2004).

Hyman et al., "What are the right targets for psychopharmacology?" Science, vol. 299, pp. 350-351, (Jan. 17, 2003).

Ibrahim et al., "Ionotropic glutamate receptor binding and subunit mRNA expression in thalmic nuclei in schizophrenia," Am. J. Psychiatry, vol. 159, No. 11, pp. 1811-1823, (Nov. 2000).

International Search Report for International Application No. PCT/JP2004/009095 dated Aug. 24, 2004.

International Search Report for International Application No. PCT/JP2011/062314 dated Jun. 28, 2011.

Ishiyama, T., et al., "Effects on sm-13496, a novel serotonin-dopamine antagonist, and other antipsychotics on cognitive performance in rat passive avoidance test," abstract, vol. 23, (2003).

Ishizumi, Kikuo, et al., "Succinimide Derivatives. II. Synthesis and Antipsychotic Activity of N-[4-[4-(1,2-Benzisothiazol-3-yl)-1-piperazinyl]butyl]-1,2-cis-cyclohexanedicarboximade (SM-9018) and Related Compounds," Chem. Pharm. Bull., vol. 43, No. 12, pp. 2139-2151, (1995).

Japanese Office Action in corresponding Japanese Application No. 2006-510283 dated May 31, 2011.

Jellinger, Kurt A., "The Pathology of Ischemic-Vascular Dementia: An Update," Journal of the Neurological Sciences 203-204, pp. 153-157, (2002).

Kahle, Philipp J. et al., "The Emerging Utility of Animal Models of Chronic Neurodegenerative Diseases," Emerging Therapeutic Targets, vol. 5, No. 1, 125-132, (2001).

Kane, John, "Commentary: Consensus statement on negative symptoms," Schizophrenia Bulletin, vol. 32, No. 2, pp. 223-224, (2006).

Kasper et al., "Cognitive effects and antipsychotic treatment," Psychoneuroendocrinology, vol. 28, pp. 27-38, (2003).

Kay, Stanley R. et al., "The Positive and Negative Syndrome Scale (PANSS) for Schizophrenia," Schizophrenia Bulletin, vol. 13, No. 2, 1987, pp. 261-276.

Kirkpatrick, Brian, et al., "The NIMH-MATRICS consensus statement on negative symptoms," vol. 32, No. 2, pp. 214-219, (2006).

Krystal et al., "NMDA receptor antagonist effects, cortical glutamatergic function, and schizophrenia: toward a paradigm shift in medication development," Psychopharmacology, vol. 169, pp. 215-233, (2003).

Laughren, Thomas, et al., "Food and Drug Administration perspective on negative symptoms in schizophrenia as a target for a drug treatment claim," Schizophrenia Bulletin, vol. 32, No. 2, pp. 220-222, (2006).

(56) References Cited

OTHER PUBLICATIONS

Lindenmayer et al., Psychiatric Quarterly, vol. 65, No. 4, pp. 299-322 (1994).
Malenka et al., "Long term potentiation—A decade of progress?" Science, vol. 285, pp. 1870-1874, (Sep. 17, 1999).
Masi, Gabriele, et al., "Aripiprazole monotherapy in children and young adolescents with perfasive development disorders," CNS Drugs, vol. 23, No. 6, pp. 511-521, (2009).
Meltzer et al., "Cognition, schizophrenia, and the atypical antipsychotic drugs," Proc. Natl. Acad. Sci., vol. 96, No. 24, pp. 13591-13593, (Nov. 23, 1999).
Mettey Y, et al., "Synthesis of 11-Aminodibenzol[b,f][1,4]thiazepines and Fluoro Derivatives," Journal of Heterocyclic Chemistry, vols. 03-04 No. 34, pp. 465-467, (1997).
Meyer, Jonathan, M. et al., "Lurasidone: a new drug in development for schizophrenia," Expert Opinion on Investigational Drugs, vol. 18, No. 11, pp. 1715-1726, (2006).
Misane et al., "Selective 5-HTIA Antagonists WAY 10065 and NAD-299 Attenuate the Impairment of Passive Avoidance Caused by Scopolamine in the Rat," Neuropsychopharmacology 28, pp. 253-264, (2003).
Miyachi, Hiroyuki et al., "Novel Biological Response Modifiers: Phthalimides with Tumor Necrosis Factor-α Production-Regulating Activity," J. Med. Chem., vol. 40, pp. 2858-2865, (1997).
Miyamoto et al., "Hyperfunction of dopaminergic and serotonergic neuronal systems in mice lacking the NMDA receptor E1 subunit," Journal of Neuroscience, vol. 21, No. 2, pp. 750-757, (Jan. 15, 2001).
Moghaddam, "Bringing order to the glutamate chaos in schizophrenia," Neuron, vol. 40, pp. 881-884, (Dec. 4, 2003).
Mohn et al., "Mice with reduced NMDA receptor expression display behaviors related to schizophrenia," Cell, vol. 98, pp. 427-436, (1999).
Myhrer, "Neurotransmitter systems involved in learning and memory in the rat: a meta-analysis based on studies of four behavioral tasks," Brain Research Reviews, vol. 41, pp. 268-287, (2003).
Nakagawa et al., "Ethanol-induced state-dependent learning is mediated by 5-hydroxytryptamine3 receptors but not by N-methyl-D-aspartate receptor complex," Brain Research, vol. 706, pp. 227-232, (1996).
New York, NY, US: Guilford Press. (1994). xii 212 pp.
Nippon-Shinkei-Seishin-Yakurigaku Zasshi (JPn. J. Neuropsychopharmacol.) 23: 296 (2003).
Noda et al, "Clozapine, but not haloperidol, reverses working memory impairment induced by chronic PCP administration in rats: a new model for cognitive dysfunction in schizophrenia," Abstracts Society Neuroscience, vol. 26, Nos. 1-2, pp. 6533, (2000).
Norman, Mark H. et al., "Effect of Linking Bridge Modifications on the Antipsychotic Profile of Some Phthalimide and Isoindolinone Derivatives," Journal of Medical Chemistry, vol. 39, No. 1, pp. 149-157, (1996).
Notice of Allowance and Fees Due in U.S. Appl. No. 12/140,927, dated Dec. 1, 2011.
Office Action in Japanese Application No. 2005-507314 dated Jun. 29, 2010 (4 pages).
Office Action in U.S. Appl. No. 10/562,039 dated Mar. 18, 2008.
Office Action in U.S. Appl. No. 10/589,804, dated Dec. 11, 2008.
Office Action in U.S. Appl. No. 12/140,927 (continuation of U.S. Appl. No. 10/562,039) dated Oct. 3, 2008.
Office Action in U.S. Appl. No. 12/401,958 (continuation of U.S. Appl. No. 10/589,804) dated Oct. 1, 2009.
Office Action in U.S. Appl. No. 12/140,927 dated Oct. 19, 2009.
Office Action in U.S. Appl. No. 12/401,958 dated Apr. 5, 2010.
Office Action in U.S. Appl. No. 12/140,927 dated Nov. 10, 2010.
Office Action in U.S. Appl. No. 13/113,703, dated Nov. 22, 2011.
Ogasa et al., "SM-13496 in patients with acute exacerbation of schizophrenia: A two-dose double-blind phase II comparison with placebo", Schizophrenia Research, vol. 60, No. 1, pp. 297, (2003).
Parnetti, et al., "Cholinergic precursors in the treatment of cognitive impairment of vascular origin: Ineffective approaches or need for re-evaluation?," Journal of the Neurological Sciences, vol. 257, pp. 264-269, (2007).
Perricone v. Medicis Pharm. Corp., 432 F.3d 1368 (Fed. Cir. 2005).
Perry, Elaine et al., "Acetylcholine in Mind: a Neurotransmitter Correlate of Consciousness?," TINS, vol. 22, No. 6, pp. 273-280 (1999).
Poster exhibited at the 18th European College of Neuropsychopharmacology Congress, Oct. 23-26, 2005.
Powell, Susan, B., et al., "RO-10-5824 is a selective dopamine D4 receptor agonist that increases novel object exploration in C57 mice," Neuropharmacology, vol. 44, pp. 473-481, (2003).
Prescribing information for "Exelon® (rivastigmine tartrate) Capsules and Oral Solution," (31 pages), (2006).
Prescribing Information for ARICEPT® (donepezil hydrochloride) (14 pages) (2010).
Protais, P. et al., "Climbing behavior induced by apomorphine in mice: a simple test for the study of dopamine receptors in striatum," Psychopharmacology, vol. 50, pp. 1-6, (1976).
Puttrese, et al., "Localized deletion of the NR1 gene in mouse prefrontal cortex impairs spatial memory," Society Neuroscience Abstract, vol. 2003, abstract No. 964.19, (2003).
Reingold, Jennifer L. et al., "Rivastigmine for the Treatment of Dementia Associated with Parkinson's Disease," Neuropsychiatric Disease and Treatment vol. 3, pp. 775-783, (2007).
Roman, Gustavo C. et al., "Donepezil in Vascular Dementia: Combined Analysis of Two Large-Scale Clinical Trials," Dementia and Geriat. Cogn. Disord., vol. 20 pp. 337-344, (2005).
Romero, Arthur G. et al., "Synthesis of Metabolically Stable Arylpiperazine 5-HT1A Receptor Agonists," Bioorganic & Medicinal Chemistry Letters, vol. 2, No. 12, pp. 1703-1706, (1992).
Russell, Vivienne, A., et al., "Animal models of attention-deficit hyperactivity disorder," Behavioral and Brain Functions, vol. 1, No. 9, pp. 1-17, (2005).
Rutten, K., et al., "Selective PDE inhibitors rolipram and sildenafil improve object retrieval performance in adult cynomolgus macaques," Psychopharmacology, vol. 196, pp. 643-648, (2008).
Sharma et al., "Cognitive function in schizophrenia deficits, functional consequences, and future treatment," Psychiatr. Clin. N. Am., vol. 26, pp. 25-40, (2003).
Shinkei Kairomo Keisei to Kofunsei Synapse Kasosei ni Kansura Kodogakuteki Kenkyu, pp. 13-2, with partial English language translation, (2003).
Small, David H., "Acetylcholinesterase Inhibitors for the Treatment of Dementia in Alzheimer's Disease: Do We Need New Inhibitors?," Expert Opinion on Emerging Drugs, vol. 10, No. 4, pp. 817-823, (2005).
Snyder, Peter J. et al., "Reversal of scopolamine-induced deficits with a single dose of donepezil, an acetylcholinesterase inhibitor," Alzheimer's & Dementia, vol. 1, pp. 126-135, (2005).
Takahashi, Satoshi et al., "Anti-Dementia Drugs and Vascular Dementia," Rinsho-Seishinigaku, (Clinical Psychiatry), vol. 31, No. 10, pp. 1189-1193, (2002).
The Lancet, "The Treatment of Senile Insanity," Lancet Limited, London, GB LNKD-DOI:10.1016/S0140-6736 (01) 05083-8, vol. 208, No. 5381, pp. 820-882, (Oct. 16, 1926).
Thomas, Elizabeth et al., "Specific Impairments in Visuospatial Working and Short-Term Memory Following Low-Dose Scopolamine Challenge in Healthy Older Adults," Neuropsychologia, vol. 46, pp. 2476-2484, (2008).
Tokita, Kenichi et al., "Combination of a Novel Antidementia Drug FK960 with Donepezil Synergistically Improves Memory Deficits in Rats," Pharmacology, Biochemistry and Behavior, vol. 73, pp. 511-519, (2002).
Tokuda, et al, "Effects of SM-13496, an atypical antipsychotic agent, on MK-801-induced learning deficit in rats," J. Pharmacol Sciences, vol. 94, supplement 1, p. 163P, (2004).
Turetsky et al., "Memory-Delineated Subtypes of Schizophrenia: Relationship to Clinical, Neuroanatomical, and Neurophysiological Measures," Neuropsychology, vol. 16, No. 4, pp. 481-490 (2002).
U.S. Appl. No. 10/562,039, filed Dec. 22, 2005.
U.S. Appl. No. 10/589,804, filed Aug. 17, 2006.

(56) References Cited

OTHER PUBLICATIONS

Wang, D., et al. "Synergistic effect of galantamine with risperidone on impairment of social interaction in phencyclidine-treated mice as a schophrenic animal model," Neuropharmacology, vol. 52, pp. 1179-1187 (2007).
Weiss et al., "The effects of second-generation antipsychotics on cognitive functioning and psychosocial outcome in schizophrenia," Psychopharmacology, vol. 162, pp. 11-17, (2002).
Wise, L.E., et al., "Reversal learning in the 8-arm radial maze in rats is impaired by subchronic adminstration of the non-competitive NMDA antagonist ketamine", Society for Neuroscience, abstract, vol. 2002, (2002).
Woolley et al., "Selective dopamine D4 receptor agonist (A-412997) improves cognitive performance and stimulates motor activity without influencing reward-related behaviour in rat," Behavioural Pharmacology, vol. 19, Iss. 8, pp. 765-776, (Dec. 2008).
Xu Taixiang et al, "Status quo and Development of Alzheimer's Disease," Acta Academiae Medicinae Qingdao Universitatis, vol. 37, No. 4, pp. 355-357, (2001).
DB Allison, et al., "Antiphychotic-induced weight gain: a comprehensive research synthesis", Am J Psychiatry, Nov. 1999; 156(11):1686-96, 2 pages.
Alp Üçok, et al., "Side effects of atypical antipsychotics: a brief overview", World Psychiatry, Feb. 2008; 7(1):58-62, 10 pages.

\* cited by examiner

AGENT FOR TREATMENT OF SCHIZOPHRENIA

This is a continuation application of application Ser. No. 10/525,021, filed Feb. 18, 2005, which is a national stage application of PCT/JP2003/010490, filed Aug. 20, 2003, and claims priority to U.S. Provisional Application 60/404,927, filed Aug. 22, 2002, the contents of which are incorporated herein by reference.

TECHNICAL FIELD

The present invention relates to a novel method for treatment of schizophrenia and a novel therapeutic agent used therein. More particularly, the present invention relates to a method for improving schizophrenia without being accompanied by extrapyramidal symptoms by orally administering a prescribed dose of a specific bicycloheptane dicarboximide derivative once a day, and a therapeutic agent used in said method.

BACKGROUND ART

Schizophrenia (split personality) is a kind of endogenous psychosis, and it is developed mainly during adolescence, and after a chronic course, the personality of patient is progressively decayed, and some of patients may culminate in a mental decay. The symptoms of this disease are, for example, positive symptoms often observed during the early stage of the disease such as hallucination, delusion, etc., or negative symptoms such as apathy and withdrawal, or cognitive dysfunction such as impairments of concentration and learning abilities, etc. Moreover, there are other symptoms such as depression, anxiety, etc. as related symptoms thereof.

Medication is mainly employed in the treatment of schizophrenia, but the treatment of schizophrenia should be continued for a long time, and even though schizophrenia is once healed, there is a large risk of reoccurring of schizophrenia after drug withdrawal so that it is necessary to continue the medication forever. Therefore, any side effects of medication may always be serious problems, and based on this perspective, it has been desired to develop a medicine being suitable for prolonged medication.

The agents for treatment of schizophrenia are various medicaments such as ones classified in the category of antipsychotic, for example, phenothiazine derivatives (e.g., chlorpromazine, methoxy-promazine, etc.), thioxanthin derivatives having a similar structure to phenothiazine (e.g., chlorprothixene, flupentixol, etc.); benzamide derivatives (e.g., sulpiride, sultopride, etc.), thienodiazepine derivatives (e.g., clotiazepam, etizolam, etc.), and further butyrophenone derivatives (e.g., haloperidol, triperidol, etc.), diphenylbutylamine derivatives (e.g., pimozide, etc.), etc.

However, phenothiazine derivatives, phenothiazine analogues, and butyrophenone derivatives may cause serious side effects of extrapyramidal symptoms showing parkinsonism such as the stiff gait of skeletal muscles, tremor of muscles, lack of facial expression, salivation, etc. Further, diphenylbutylamine derivatives may cause extrapyramidal symptoms in addition to insomnia. In addition, these conventional antipsychotics may be effective on only some of symptoms among positive symptoms, negative symptoms, cognitive dysfunctions of schizophrenia, and there has been no drug being effective on all of these symptoms.

Therefore, it has been desired to develop a safe medicament which exhibits an excellent effect on various schizophrenia as an antipsychotic without causing side effects such as extrapyramidal symptoms.

On the other hand, it has been known that the imide derivative of the following formula, which was found by the co-workers of the present inventors, may be useful as an antipsychotic (c.f., neuroleptic agent, antiaxiety, etc.), especially as an agent for treatment of schizophrenia, senile insanity, manic depressive psychoses, and nervous breakdown (U.S. Pat. No. 5,532,372).

wherein Z is

D is a group of the formula: $-(CH_2)_p-A-(CH_2)_q-$, etc., and
Ar is an aromatic group, or an aromatic heterocyclic group, etc.

DISCLOSURE OF INVENTION

The present inventor has intensively studied on a series of imide derivatives with respect to many aspects including a use and a dose thereof in order to find a novel agent for treatment of schizophrenia, which may exhibit an excellent effect in the treatment of schizophrenia and have no side effect such as extrapyramidal symptoms, which are often observed in many conventional antipsychotics, and can safely be administered for a long time. As a result, the present inventors have found that (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptane-dicarboximide of the following formula:

(1)

or a pharmaceutically acceptable salt thereof such as a hydrochloride thereof is effective for relieving the wide-ranging symptoms of schizophrenia, and may treat schizophrenia quite safely without being accompanied by extrapyramidal symptoms by orally administering a prescribed dose thereof once a day.

Namely, the present invention provides a method for treatment of schizophrenia without being accompanied by extrapyramidal symptoms by orally administration of a prescribed amount of (1R,2S,3R,4S)-N-[(1R,2R)-2-[4-(1,2-benzoisothiazol-3-yl)-1-piperazinyl-methyl]-1-cyclohexyl-methyl]-2,3-bicyclo[2.2.1]heptanedicarboximide of the above formula (1) or a pharmaceutically acceptable salt thereof once a day, and further provides an agent for treatment of schizophrenia which is used in said method.

DETAILED DESCRIPTION OF INVENTION

As shown in Examples as described hereinafter, when orally administering a prescribed dose of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride once a day for 6 weeks to the patients with schizophrenia in the acute exacerbation, the present inventors have found that the excellent effects on the wide-ranging symptoms were obtained, and surprisingly, any extrapyramidal symptoms as observed in the conventional antipsychotics were hardly observed, especially, abnormal electrocardiogram which progresses to sudden death is not recognized, and hence, that this compound may be quite safely used in the treatment of schizophrenia.

Namely, the present invention provides a novel method for treatment of schizophrenia improving a wide-ranging schizophrenia including positive symptoms, negative symptoms, and cognitive dysfunction, especially positive symptoms and negative symptoms, without being accompanied by extrapyramidal symptoms which comprises orally administering a prescribed dose of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide of the above formula (1) or a pharmaceutically acceptable salt thereof, especially a hydrochloride thereof, to a patient with schizophrenia once a day.

The present invention also provides a novel agent for treatment of such schizophrenia.

According to the present invention, excellent improving effects on the wide-ranging symptoms of schizophrenia may be obtained by orally administering (1R,2S3R,4S)-N-[(1R,2R)-2-[4-(1,2-benzoisothiazol-3-yl) -1-piperazinylmethyl]-1-cyclohexylmethyl]-2,3-bicyclo[2.2.1]-heptanedicarboximide or a pharmaceutically acceptable salt thereof, for example, a hydrochloride, at a daily dose of 5 mg to 120 mg, preferably at a daily dose of 10 mg to 100 mg, more preferably at a daily dose of 20 mg to 80 mg, once a day. Further, in the therapeutic method of the present invention, side effects such as extrapyramidal symptoms such as parkinsonism, dyskinesia, akathisia, etc., abnormal electrocardiogram, hepatic dysfunction are hardly observed, and hence, the present method may be quite safely used and suitable for a prolonged medication.

Besides, when the present method is applied to a patient with schizophrenia in chronic phase, the above active compound should preferably be administered to said patient for a long time at a dose as low as possible, and in such a case, the daily dose of the active compound is in the range of 5 mg to 80 mg, preferably in the range of 5 mg to 60 mg, more preferably in the range of 10 mg to 40 mg, and it is orally administered once a day.

The therapeutic agent used in the method for treatment of schizophrenia of the present invention is in the form of an oral preparation, which contains the compound of the above formula (1) or a pharmaceutically acceptable salt thereof, especially (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride in an amount of 5 mg to 120 mg, preferably in an amount of 10 mg to 100 mg, more preferably in an amount of 20 mg to 80 mg per a single dosage unit. The oral preparation includes, for example, tablets, granules, fine granules, powders, capsules, syrups, etc. These preparations should be in the form of a preparation for administration once a day.

The above preparations may be prepared by a conventional method by using a conventional pharmaceutically acceptable carrier which is usually used in the preparation of a conventional pharmaceutical formulation, for example, excipients such as lactose, white sugar, glucose, starch, calcium carbonate, kaolin, talc, crystalline cellulose, silicic acid, etc, binders such as water, ethanol, gelatin, carboxymethylcellulose, shellac, methylcellulose, gum arabic, tragacanth powder, polyvinylpyrrolidone, etc., disintegrating agents such as sodium arginate, agar powder, laminaran powder, sodium hydrogen carbonate, polyoxyethylenesorbitan fatty acid esters, sodium laurylsulfate, stearic acid monoglyceride, etc., lubricants such as purified talc, stearate, boric acid powder, polyethyleneglycol, etc.

EXPERIMENTS

The method for treatment of the present invention and the effects thereof are illustrated in more detail by Experiments as described hereinafter.

The active compound SM-13496 used in Experiments means (1R,2S,3R,4S)-N-1[(1R,2R)-2-[4-(1,2-benzoisothiazol-3-yl)-1-piperazinyl-methyl]-1-cyclohexylmethyl]-2,3-bicyclo[2.2.1]heptanedicarboximide hydrochloride, and the meanings of the abbreviations used in Experiments are as follows.

DSM-IV: Diagnostic and Statistical Manual of Mental Disorders, 4th ed.
CGI-S; Clinical Global Impressions scale-Severity of Illness
CGI-I: Clinical Global Impressions scale-Improvement
AIMS: Abnormal Involuntary Movement Scale
EPS: Extrapyramidal symptoms
LOCF: Last Observation Carried Forward (LOCF Analysis: a method of using last not-missing data in cases of dropouts)
BAS: Barnes Akathisia Scale
SAS: Simpson-Angust Rating Scale (Rating Scale For Extrapyramidal Reactions)
PANSS: Positive and Negative Syndrome Scale (Rating Scale For Positive Negative symptoms)

Experiment 1

First Stage Phase II Clinical Trial (1) Test Method

According to the procedures as shown in Table 1 as described below, the placebo-controlled double blind experiment was done on 149 patients with schizophrenia in the acute exacerbation phase at 15 facilities in USA. The efficacy and safeness were studied when SM-13495 at a dose of 40 mg or 120 mg, or a placebo was orally administered once a day for 6 weeks after placebo washout.

TABLE 1

| | |
|---|---|
| Name of Clinical Trial | A double-blind, randomized, fixed dose, placebo-controlled, parallel-group, 6-week, efficacy, safety, and tolerability study of two dose levels of SM-13496 in patients with schizophrenia by DSM-IV criteria who are experiencing an acute exacerbation of symptoms |
| Purpose | The efficacy and safety on patients with schizophrenia in the acute exacerbation phase (DSM-IV criteria) were studied in the placebo-controlled, parallel-group, double-blind test. |
| Subjects | Selection criteria:<br>1) Patients with scchizophrenia determined according to DSM-IV criteria who are experiencing an acute exacerbation of symptoms<br>2) Patients having 42 or more of Extracted-BPRS Score as well as 4 or more of CGI-S Score<br>3) Patients having less than 2 of Simpson-Angus Score as well as less than 3 of AIMS Score<br>4) Patients suffering from schizophrenia for more than 1 year<br>5) Males and females aged 18-64 years<br>Factors for patient exclusion:<br>1) Patients with treatment-resistant schizophrenia<br>2) Patients being taking depot injections before finishing the therapy cycle<br>3) Patients having a strong suicidal ideation<br>4) Patients with Parkinson's disease, Alzheimer disease, drug addiction, convulsive disorders, epilepsy<br>5) Pregnant women and any women having a possilbility of pregnancy, and lactating women<br>6) Patients having drug hypersensitivity<br>7) Any patients who are examined not to be suitable as subjects by principal investigator |
| Design of Clinical Trial | Placebo-controlled, randomized, comparison with parallel-group, double-blind |
| Dosage and Administration route | Oral administration of the test compound at a dose of 40 mg/day, 120 mg/day or a placebo once a day for 6 weeks<br>Washout with placebo for one week (at least for 3 day)<br>Hospitalization during the washout period and two weeks after medication |
| Combined Drug and Combination Therapy | 1) Another antipsychotic is not administered. When another antipsychotic is taken, then it is necessary to set up a washout period before the trial at least 3 days for oral drug or for one therapy cycle for depot injection.<br>2) In case of onset of extrapyramidal symptoms, then the administration of an antiparkinson agent is allowed.<br>3) In case of onset of insomnia, lorazepam is used. |
| Number of subjects | In the planning stages: 132 subjects (each 44 subjects for the placebo-treated group, the 40 mg-treated group and the 120 mg-treated group)<br>After the completion of the trial: 149 subjects (50 subjects for the placebo-treated group, 50 subjects for the 40 mg-treated group, and 49 subjects for the 120 mg-treated group) |
| Evaluation Items | Efficacy: PANSS, Extracted-BPRS, CGI-S/I<br>Safety: EPS Rating scale (Simpson-Angus, Barnes, AIMS), vital signs (body temperature, blood pressure, pulse), 12-lead electrocardiogram, laboratory test [hematologic test, biochemical test of blood, prolactin, urine test] psychosomatic conditions, eyeground-slit-lamp microscopy, adverse event |

(2) Test Results:

1) Evaluation of Efficacy:

(i) The data by BPRS and PANSS (LOCF), and CGI-S and CGI-I at the end of the trial are shown in Table 2 and Table 3, respectively. As is shown in Table 2 and Table 3, the reductions in the scores at the end of the trial (6 weeks after the administration) from those prior to the administration in the groups treated by SM-13496 40 mg or 120 mg are statistically significant as compared to that in the placebo-treated group with respect to BPRS, CGI-I and CGI-S evaluations. With respect to PANSS evaluation, the reduction in the score at the end of the experiment in the SM-13496 120 mg-treated group is statistically significant as compared to that in the placebo-treated group, which means the psychotic manifestations are improved by SM-13496.

TABLE 2

| | Dose (No. of Subjects) | | | | |
|---|---|---|---|---|---|
| | Placebo (45) | SM-13496 40 mg (47) | | SM-13496 120 mg (44) | |
| Rating scale | Average (SD) | Average (SD) | p value[#] | Average (SD) | p value[#] |
| BPRS Total Score | −4.0 (8.45) | −10.0 (12.79) | 0.014 | −11.3 (8.89) | 0.003 |
| PANSS Total Score | −5.8 (14.06) | −14.1 (23.10) | 0.063 | −17.4 (15.70) | 0.010 |

[#]Two-sided Dunnett's t-test (comparison between the groups treated by each dose and the placebo-treated group)
Covariance analysis using faculty and Groups as factors and the values before administration as covariate

TABLE 3

| | Dose | | | | |
|---|---|---|---|---|---|
| | Placebo | SM-13496 40 mg | | SM-13496 120 mg | |
| Rating Scale | Average (SD) | Average (SD) | p value[#] | Average (SD) | p value[#] |
| CGI-S | (n = 41) 0.0 (0.77) | (n = 41) −0.7 (1.12) | 0.004 | (n = 40) −0.8 (1.03) | 0.002 |
| CGI-I | (n = 45) 4.0 (1.41) | (n = 47) 3.2 (1.56) | 0.013 | (n = 42) 3.0 (1.29) | 0.005 |

Figure 1:
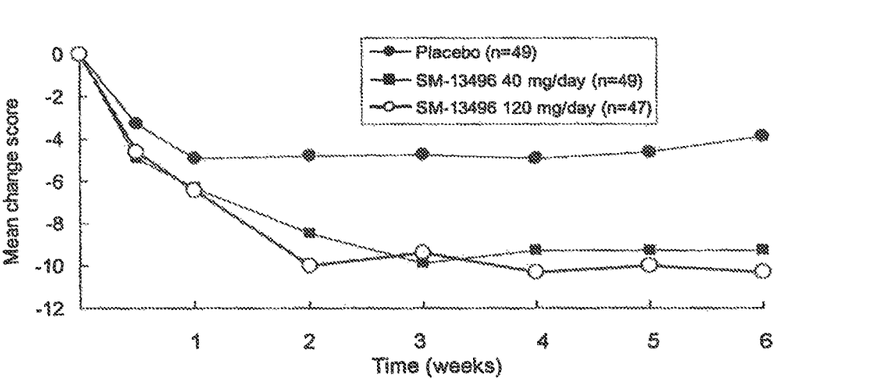
FIG. 1 is a graph showing the change with time in scores of Brief Psychiatric Rating Scale: BPRS, which are indexes for the effects on schizophrenia, of the active compound of the present invention, (1R,2 S,3R,4 S)-N-[(1R,2R)-2-[4-(1,2-benzoisothiazol-3 -yl)-1-piperazinyl-methyl]-1-cyclohexylmethyl]-2,3-bicyclo[2.2.1]heptanedicarboximide hydrochloride and placebo in the double blind clinical trial.

[#]Two-sided Dunnett's t-test (comparison between the groups treated by each dose and the placebo-treated group)
Covariance analysis using faculty and Groups as factors and the values before administration as covariate (ii) Further, the appended FIG. 1 shows the changes in BPRS total score (LOCF). As is shown in FIG. 1, the BPRS scores in the SM-13496-treated groups are statistically significantly reduced from those of prior to the administration as compared to that in the placebo-treated group at the 2 weeks or later ($p<0.05$).

(iii) The ratio of the patients of which the BPRS reduction at the end of the experiment is 20% or more, or the patients who showed 1 or 2 of CGI-I, those patients are considered as responder, is shown in Table 4. As is apparent from Table 4, there was a statistically significant difference between the SM-13496 40 mg- or 120 mg-treated group and the placebo-treated group.

TABLE 4

| | Dose (No. of Subjects) | | | | |
|---|---|---|---|---|---|
| | Placebo (45) | SM-13496 40 mg (47) | | SM-13496 120 mg (44) | |
| | Number | Number | p value# | Number | p value# |
| Responder | 10 | 26 | 0.002 | 22 | 0.007 |

Cochran-Mantel-Haenszel test adjusting the faculties (comparison between the groups treated by each dose and the placebo-treated group)

2) Evaluation of Safety:
(i) Adverse events observed in 10% or more of the patients are shown in Table 5.

TABLE 5

| | Placebo | 40 mg | 120 mg |
|---|---|---|---|
| Number of Subjects | 50 | 50 | 49 |
| Number of subjects showing adverse events (%) | 36 (72) | 40 (80) | 38 (78) |
| Number of subjects showing serious adverse events (%) | 3 (6) | 3 (6) | 3 (6) |
| Number of subjects who drop out from the trial due to adverse events (%) | 2 (4) | 6 (12) | 6 (12) |
| Occurrence of Adverse events (%) | | | |
| Digestive disturbance | 6 (12) | 4 (8) | 2 (4) |
| Nausea | 2 (4) | 5 (10) | 11 (22) |
| Headache | 5 (10) | 8 (16) | 3 (6) |
| Akathisia | 0 (0) | 4 (8) | 7 (14) |
| Free-floating vertigo (excluding rotatory vertigo) | 3 (6) | 6 (12) | 5 (10) |
| Suppression | 5 (10) | 9 (18) | 7 (14) |
| Drowsiness | 2 (4) | 4 (8) | 5 (10) |
| Exacerbation of schizophrenia | 5 (10) | 2 (4) | 1 (2) |

Subject having multiple adverse events was accounted as 1.

As is shown in Table 5, 114 subjects among 149 subjects (77%) showed adverse events, but most of them were mild or moderate ones. The number of subjects who dropped out from the trial due to the adverse events was higher in both of the groups treated by two doses of SM-13496 than in the placebo-treated group.

The main adverse events are suppression, nausea, headache, akathisia, and free-floating vertigo (excluding rotatory vertigo). The ratio of the subjects showing suppression was 10%, 18%, 14% in the placebo-treated group, the SM-13496 40 mg-treated group, and the SM-13496 120 mg-treated group, respectively. In the SM-13496 120 mg-treated group, nausea was more observed as compared to the other groups, but digestive disturbance was less observed than in the placebo-treated group. Exacerbation of schizophrenia was less observed in the SM-13496 40 mg- and 120 mg-treated groups (4% and 2%, respectively) than in the placebo-treated group (10%). Akathisia was observed only in the SM-13496 treated groups, Le., 8% and 14% in the 40 mg-treated group and in the 120 mg-treated group, respectively. The occurrence of the adverse events in the groups treated by SM 13496 were the same as that in the placebo-treated group. Either body weight gain, bulimia, impotence, erectile dysfunction or convulsion was not observed.

(ii) The serious adverse events observed in the above phase II clinical trial are shown in Table 6 as described below.

TABLE 6

| | Placebo | 40 mg | 120 mg |
|---|---|---|---|
| Number of Subjects | 50 | 50 | 49 |
| Total (%) | 4 (8) | 3 (6) | 2 (4) |
| Occurrence of Serious Adverse Events (%) | | | |
| Exacerbation of paranoia | 0 (0) | 1 (2) | 0 (0) |
| Psychosis aggravated | 0 (0) | 1 (2) | 0 (0) |
| Exacerbation of schizophrenia | 4 (8) | 1 (2) | 1 (2) |
| Paranoid schizophrenia | 0 (0) | 0 (0) | 1 (2) |

As is shown in Table 6 the serious adverse events were observed in 4 cases of the placebo-treated group, 3 cases of the SM-13496 40 mg-treated group and 2 cases of the SM 13496 120 mg-treated group, but the relationship to the tested medicament was denied.

(iii) Further, the side effects observed in this clinical trial are listed in the following Table 7.

TABLE 7

| | Placebo | 40 mg | 120 mg |
|---|---|---|---|
| Number of Subjects | 50 | 50 | 49 |
| Occurrence of side effects (%) | 22 (44) | 33 (66) | 35 (71) |
| Mental disturbance | | | |
| Restlessness | 0 (0) | 1 (2) | 1 (2) |
| Psychosis aggravated | 0 (0) | 0 (0) | 2 (4) |
| Agitation | 0 (0) | 0 (0) | 1 (2) |
| Agitation aggravated | 0 (0) | 0 (0) | 2 (4) |
| Anxiety aggravated | 0 (0) | 1 (2) | 0 (0) |
| Insomnia | 0 (0) | 1 (2) | 1 (2) |
| Exacerbation of insomnia | 0 (0) | 0 (0) | 1 (2) |
| Nightmare | 0 (0) | 0 (0) | 1 (2) |
| Metabolic disturbances and nutritional disturbance | | | |
| Anorexia | 1 (2) | 1 (2) | 0 (0) |
| Decrease in appetite | 1 (2) | 1 (2) | 1 (2) |
| Disturbance in Skin and Hypodermis | | | |
| Pruritus | 1 (2) | 0 (0) | 0 (0) |
| Infection and parasitosis | | | |
| Tinea pedis | 0 (0) | 0 (0) | 1 (2) |
| External otitis | 0 (0) | 1 (2) | 0 (0) |
| Parotiditis | 1 (2) | 0 (0) | 0 (0) |
| Urinary tract infection | 0 (0) | 1 (2) | 0 (0) |
| Vascular diseases | | | |
| Flushing | 1 (2) | 0 (0) | 0 (0) |
| Hot flashes | 0 (0) | 0 (0) | 1 (2) |
| Disturbance in respiratory organ, chest and mediastinum | | | |
| Laryngopharynx pain | 0 (0) | 1 (2) | 0 (0) |
| Breathing difficulty | 0 (0) | 0 (0) | 1 (2) |
| Heart problems | | | |
| Sinus tachycardia | 0 (0) | 0 (0) | 1 (2) |
| Palpitation | 0 (0) | 0 (0) | 1 (2) |
| Gastroenteric disturbance | | | |
| Nausea | 2 (4) | 4 (8) | 9 (18) |
| Vomiting | 0 (0) | 2 (4) | 3 (6) |
| Constipation | 1 (2) | 2 (4) | 0 (0) |
| Diarrhea | 3 (6) | 3 (6) | 0 (0) |
| Loose stools | 0 (0) | 0 (0) | 1 (2) |

TABLE 7-continued

|  | Placebo | 40 mg | 120 mg |
|---|---|---|---|
| Tongue disturbance | 0 (0) | 1 (2) | 0 (0) |
| Dyspepsia | 2 (4) | 3 (6) | 2 (4) |
| Flatulence | 0 (0) | 1 (2) | 0 (0) |
| Dry mouth | 1 (2) | 0 (0) | 0 (0) |
| Salivary hypersecretion | 1 (2) | 0 (0) | 0 (0) |
| Abdominal pain | 2 (4) | 0 (0) | 0 (0) |
| Total disability and local condition | | | |
| Fatigue | 3 (6) | 3 (6) | 1 (2) |
| Fatigue aggravated | 0 (0) | 1 (2) | 0 (0) |
| Hot sensation | 1 (2) | 0 (0) | 0 (0) |
| Sleepiness | 1 (2) | 1 (2) | 2 (4) |
| Nervous system disorder | | | |
| Suppression | 3 (6) | 9 (18) | 7 (14) |
| Akathisia | 0 (0) | 4 (8) | 7 (14) |
| Free-floating vertigo (excluding rotatory vertigo) | 0 (0) | 5 (10) | 5 (10) |
| Drowsiness | 2 (4) | 4 (8) | 5 (10) |
| Headache | 3 (6) | 6 (12) | 1 (2) |
| Extrapyramidal disease | 0 (0) | 1 (2) | 3 (6) |
| Tremor | 0 (0) | 3 (6) | 3 (6) |
| Akathisia aggravated | 0 (0) | 1 (2) | 0 (0) |
| Dystonic reaction | 0 (0) | 1 (2) | 0 (0) |
| Anarthria | 0 (0) | 0 (0) | 1 (2) |
| Glossoplegia | 1 (2) | 0 (0) | 0 (0) |
| Cogwheel rigidity | 0 (0) | 0 (0) | 1 (2) |
| Trismus | 0 (0) | 0 (0) | 1 (2) |
| Musculoskeletal system and connective tissue disorder | | | |
| Muscle stiffness | 1 (2) | 2 (4) | 1 (2) |
| Myalgic pain | 0 (0) | 0 (0) | 1 (2) |
| Cervical rigidity | 0 (0) | 1 (2) | 0 (0) |
| Articular rigidity | 0 (0) | 1 (2) | 0 (0) |
| Melalgia | 0 (0) | 0 (0) | 1 (2) |
| Heavy feeling | 0 (0) | 1 (2) | 0 (0) |
| Laboratory assay | | | |
| Increase in prolactin level in the blood | 0 (0) | 1 (2) | 1 (2) |
| Increase in creatine phosphokinase level in the blood | 0 (0) | 1 (2) | 0 (0) |
| Abnormal electrocardiogram | 1 (2) | 0 (0) | 0 (0) |
| Weight loss | 1 (2) | 1 (2) | 2 (4) |
| Increase in total protein | 0 (0) | 1 (2) | 0 (0) |
| Abnormal liver function tests | 0 (0) | 0 (0) | 1 (2) |
| Renal Injury and urinary disorder | | | |
| Polyuria | 1 (2) | 0 (0) | 0 (0) |
| Frequent urination | 1 (2) | 0 (0) | 0 (0) |
| Ocular disturbance | | | |
| Blurred vision | 0 (0) | 1 (2) | 1 (2) |
| Dry eye | 1 (2) | 0 (0) | 0 (0) |

As is shown in Table 7, among the adverse events, the main side effects, a relationship of which to the SM-13496 cannot be denied, was suppression, nausea, akathisia, free-floating vertigo (excluding rotatory vertigo), sleepiness, headache. The occurrence of dystonic reaction was low (less than 4%) in the SM-13496-treated groups. There was no clinically significant change in 12-lead electrocardiogram. There was no significant difference in the ratio of the patients having an abnormal change in laboratory values among the groups. In the SM-13496-treated groups, the moderate increase in the prolactin level in the blood was observed, but there was no clinically significant change in the body temperature, respiration rate, funduscopic examination and slit-lamp microscopy.

(iv) Further, the results of the evaluation for dyskinesia (by AIMS), akathisia (by BAS), parkinsonism (by SAS), those symptoms being extrapyramidal symptoms, are shown in Table 8.

TABLE 8

|  | Placebo* | SM-13496 40 mg* | | SM-13496 120 mg* | |
|---|---|---|---|---|---|
| Rating Scale | Average (SD) | Average (SD) | p value[#] | Average (SD) | p value[#] |
| AIMS | 0.7 (2.63) | 0.7 (2.88) | 0.978 | 0.2 (2.21) | 0.467 |
| BAS** | 0.0 (0.97) | 0.1 (1.04) | 0.687 | 0.4 (0.94) | 0.352 |
| SAS | −0.1 (0.96) | 0.1 (1.08) | 0.588 | 0.1 (1.11) | 0.808 |

[#]Two-sided Dunnett's t-test (comparison between the groups treated by each dose and the placebo-treated group)
Covariance analysis using faculty and Groups as factors and the values before administration as covariate
*n = 44-47 for each rating score
**BAS Global score As is apparent from the results in Table 8, there was no significant difference in the changes in the score prior to the treatment or in the total score between the treated groups. The ratio of the patients requiring benztropine was 24% in the SM-13496-treated groups and 18% in the placebo-treated group.

INDUSTRIAL APPLICABILITY

The method for treatment of schizophrenia and the agent intended to be used therein of the present invention exhibit an excellent effect on the improvement of wide-ranging schizophrenia including positive symptoms, negative symptoms, cognitive dysfunctions, especially positive symptoms and negative symptoms, without accompanied by extrapyramidal symptoms by orally administering a prescribed amount of (1R,2S,3R,4S)-N-[(1R,2R)-2-[4-(1,2-benzo-isothiazol-3-yl)-1-piperazinylmethyl]-1-cyclohexylmethyl-2,3-bicyclo-2.2.1]heptanedicarboximide or a pharmaceutically acceptable salt thereof, especially a hydrochloride thereof once a day to a patient with schizophrenia. Besides, since the present method and the agent used therein do not cause an abnormal electrocardiogram which may progress to sudden death, or do not show excessive suppression effects, they may be quite safely employed and may be suitable even to a prolonged medication, and further they may be applied safely to even elder patients, and hence, the present method and the agent used therein are extremely excellent.

The invention claimed is:

1. A method for treating schizophrenia in a patient without a clinically significant weight gain, comprising:
    administering orally to the patient (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide or a pharmaceutically acceptable salt thereof at a dose of from 20 to 120 mg/day such that the patient does not experience a clinically significant weight gain.

2. The method of claim 1, wherein (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride is administered.

3. The method of claim 2, wherein the administering is conducted such that the patient does not experience a clinically significant weight gain after six weeks of administration.

4. The method of claim 3, wherein the administering is conducted without concurrently administering another antipsychotic medication.

5. The method of claim 2, further comprising:
detecting a weight gain after six weeks of administration.

6. The method of claim 1, wherein said patient has a BPRS score of at least 42 and wherein the patient's BPRS score is significantly reduced from a baseline measurement prior to the administering.

7. The method of claim 3, wherein the dose is from 40 to 120 mg once daily.

8. A method for treating manic depressive psychosis in a patient without a clinically significant weight gain, comprising:
administering orally to the patient (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide or a pharmaceutically acceptable salt thereof at a dose of from 20 to 120 mg/day such that the patient does not experience a clinically significant weight gain.

9. The method of claim 8, wherein (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride is administered.

10. The method of claim 9, wherein the administering is conducted such that the patient does not experience a clinically significant weight gain after six weeks of administration.

11. The method of claim 9, further comprising:
detecting a weight gain after six weeks of administration.

12. The method of claim 10, wherein the administering is conducted without concurrently administering another antipsychotic medication.

13. The method of claim 10, wherein the dose is 20 mg once daily.

14. The method of claim 10, wherein the dose is 40 mg once daily.

15. The method of claim 10, wherein the dose is 60 mg once daily.

16. The method of claim 10, wherein the dose is 80 mg once daily.

17. The method of claim 10, wherein the dose is 120 mg once daily.

18. The method of claim 9, wherein the dose is 20 mg, 40 mg, 60 mg, 80 mg or 120 mg once daily.

19. The method of claim 3, wherein the dose is 20 mg once daily.

20. The method of claim 3, wherein the dose is 40 mg once daily.

21. The method of claim 3, wherein the dose is 60 mg once daily.

22. The method of claim 3, wherein the dose is 80 mg once daily.

23. The method of claim 3, wherein the dose is 120 mg once daily.

24. The method of claim 2, wherein the dose is 20 mg, 40 mg, 60 mg, 80 mg or 120 mg once daily.

25. A method of treating a patient with an antipsychotic without a clinically significant weight gain in the patient, comprising:
orally administering the antipsychotic to the patient once daily at a dose of from 20 to 120 mg such that the patient does not experience a clinically significant weight gain,
wherein the antipsychotic is (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide or a pharmaceutically acceptable salt thereof.

26. The method of claim 25, wherein the antipsychotic is (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

27. The method of claim 26, wherein the administering is conducted such that the patient does not experience a clinically significant weight gain after six weeks of administration.

28. The method of claim 26, further comprising:
detecting a weight gain after six weeks of administration.

29. The method of claim 27, wherein the method treats schizophrenia in the patient.

30. The method of claim 27, wherein the method treats manic depressive psychosis in the patient.

31. The method of claim 25, wherein the method treats the patient without the patient experiencing a weight gain.

32. The method of claim 29, wherein the administering is conducted without concurrently administering another antipsychotic medication.

33. The method of claim 30, wherein the administering is conducted without concurrently administering another antipsychotic medication.

34. The method of claim 27, wherein the dose is 20 mg.

35. The method of claim 27, wherein the dose is 40 mg.

36. The method of claim 27, wherein the dose is 60 mg.

37. The method of claim 27, wherein the dose is 80 mg.

38. The method of claim 27, wherein the dose is 120 mg.

39. The method of claim 26, wherein the dose is 20 mg, 40 mg, 60 mg, 80 mg or 120 mg.

40. A method of treating a patient with an antipsychotic without a clinically significant weight gain, comprising:
orally administering once daily to the patient a pharmaceutical composition comprising 20 to 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide or a pharmaceutically acceptable salt thereof as a sole active ingredient such that the patient does not experience a clinically significant weight gain.

41. The method of claim 40, wherein the sole active ingredient is (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

42. The method of claim 41, wherein the pharmaceutical composition is a tablet.

43. The method of claim 41, wherein the administering is conducted such that the patient does not experience a clinically significant weight gain after six weeks of administration.

44. The method of claim 41, further comprising:
detecting a weight gain after six weeks of administration.

45. The method of claim 43, wherein the method treats schizophrenia in the patient.

46. The method of claim 43, wherein the method treats manic depressive psychosis in the patient.

47. The method of claim 45, wherein the administering is conducted without concurrently administering another antipsychotic medication.

48. The method of claim 46, wherein the administering is conducted without concurrently administering another antipsychotic medication.

49. The method of claim 41, wherein the pharmaceutical composition includes 40 to 120 mg of (1R,2S,3R,4S)-N-

[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

50. The method of claim 41, wherein the pharmaceutical composition includes 20 mg, 40 mg, 60 mg, 80 mg or 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

51. The method of claim 41, wherein the pharmaceutical composition includes 20 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

52. The method of claim 41, wherein the pharmaceutical composition includes 40 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

53. The method of claim 41, wherein the pharmaceutical composition includes 60 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

54. The method of claim 41, wherein the pharmaceutical composition includes 80 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

55. The method of claim 41, wherein the pharmaceutical composition includes 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

56. A method of treating a patient with an antipsychotic without a weight gain, comprising:
orally administering once daily to the patient a pharmaceutical composition comprising 20 to 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide or a pharmaceutically acceptable salt thereof as a sole active ingredient such that the patient does not experience a weight gain.

57. The method of claim 56, wherein the sole active ingredient is (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

58. The method of claim 57, wherein the pharmaceutical composition is a tablet.

59. The method of claim 57, wherein the administering is conducted such that the patient does not experience a weight gain after six weeks of administration.

60. The method of claim 57, further comprising:
detecting a weight gain after six weeks of administration.

61. The method of claim 57, wherein the method treats schizophrenia in the patient.

62. The method of claim 57, wherein the method treats manic depressive psychosis in the patient.

63. The method of claim 61, wherein the administering is conducted without concurrently administering another antipsychotic medication.

64. The method of claim 62, wherein the administering is conducted without concurrently administering another antipsychotic medication.

65. The method of claim 61, wherein the pharmaceutical composition includes 40 to 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

66. The method of claim 57, wherein the pharmaceutical composition includes 20 mg, 40 mg, 60 mg, 80 mg or 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

67. The method of claim 62, wherein the pharmaceutical composition includes 20 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

68. The method of claim 61, wherein the pharmaceutical composition includes 40 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

69. The method of claim 62, wherein the pharmaceutical composition includes 40 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

70. The method of claim 61 wherein the pharmaceutical composition includes 60 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

71. The method of claim 62 wherein the pharmaceutical composition includes 60 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

72. The method of claim 61, wherein the pharmaceutical composition includes 80 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

73. The method of claim 62, wherein the pharmaceutical composition includes 80 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

74. The method of claim 61, wherein the pharmaceutical composition includes 120 mg of (1R,2S,3R,4S)-N-[(1R,2R)-2-[4-(1,2-benzoisothiazol-3-yl)-1-piperazinylmethyl]-1-cyclohexylmethyl]-2,3-bicyclo[2.2.1]heptanedicarboximide hydrochloride.

75. The method of claim 62, wherein the pharmaceutical composition includes 120 mg of (1R,2S,3R,4S)-N-[(1R,2R)-2-[4-(1,2-benzoisothiazol-3-yl)-1 -piperazinylmethyl]-1-cyclohexylmethyl]-2,3-bicyclo[2.2.1]heptanedicarboximide hydrochloride.

* * * * *